(12) United States Patent
Zhou et al.

(10) Patent No.: US 9,196,424 B2
(45) Date of Patent: Nov. 24, 2015

(54) DOUBLE-CENTER BIPYRIDYL CATIONIC ION LIQUID, PREPARATION METHOD THEREFOR AND USE THEREOF

(75) Inventors: Mingjie Zhou, Shenzhen (CN); Daxi Liu, Shenzhen (CN); Yaobing Wang, Shenzhen (CN)

(73) Assignee: OCEAN'S KING LIGHTING SCIENCE & TECHNOLOGY CO., LTD., Shenzhen, Guangdong (CN)

( * ) Notice: Subject to any disclaimer, the term of this patent is extended or adjusted under 35 U.S.C. 154(b) by 180 days.

(21) Appl. No.: 14/234,384

(22) PCT Filed: Aug. 30, 2011

(86) PCT No.: PCT/CN2011/079118
§ 371 (c)(1),
(2), (4) Date: Jan. 22, 2014

(87) PCT Pub. No.: WO2013/029237
PCT Pub. Date: Mar. 7, 2013

(65) Prior Publication Data
US 2014/0166921 A1    Jun. 19, 2014

(51) Int. Cl.
| | | |
|---|---|---|
| *C07D 401/04* | (2006.01) |
| *C08K 5/3432* | (2006.01) |
| *H01G 9/035* | (2006.01) |
| *H01M 10/052* | (2010.01) |
| *H01M 10/0569* | (2010.01) |
| *C07D 213/22* | (2006.01) |
| *H01G 11/60* | (2013.01) |
| *H01G 11/58* | (2013.01) |

(52) U.S. Cl.
CPC .............. *H01G 9/035* (2013.01); *C07D 213/22* (2013.01); *H01G 11/58* (2013.01); *H01G 11/60* (2013.01); *H01M 10/052* (2013.01); *H01M 10/0569* (2013.01); *C08K 5/3432* (2013.01); *H01M 2300/0037* (2013.01); *H01M 2300/0045* (2013.01); *Y02E 60/122* (2013.01)

(58) Field of Classification Search
CPC .................. H01M 2300/0045; H01M 10/052; H10G 9/035; Y02E 60/122; C07D 213/22; C08K 5/3432
See application file for complete search history.

(56) References Cited

U.S. PATENT DOCUMENTS

| | | | | |
|---|---|---|---|---|
| 3,854,794 A | * | 12/1974 | Van Dam | ............. G02F 1/1521 359/272 |
| 4,194,046 A | * | 3/1980 | Junghans | ................. C25B 3/04 546/259 |
| 6,855,850 B2 | * | 2/2005 | Adachi | ................... C07B 39/00 544/336 |
| 2004/0199015 A1 | | 10/2004 | Yuyama et al. | |

FOREIGN PATENT DOCUMENTS

| | | |
|---|---|---|
| CN | 1326936 A | 12/2001 |
| CN | 1838469 A | 9/2006 |
| EP | 1707265 A1 | 10/2006 |
| EP | 1837333 A1 | 9/2007 |
| JP | S54-143783 A | 11/1979 |
| JP | 62-175463 * | 8/1987 |
| JP | 2002151360 A | 5/2002 |
| JP | 2004-29433 * | 1/2004 |
| WO | WO/2004/001877 A | 12/2003 |

OTHER PUBLICATIONS

Chandrasekaran K. et al. Photoelectrochemical Cells Based on Hydrogen-Atom Abstraction and Electron-Transfer Reactions in Solution: Systems Based on Benzophenone, 2-Propanol, Trialkylamines, and Methyl Viologen. J. Am. Chem. SOC. 1981, vol. 103, pp. 1270-7215.

* cited by examiner

*Primary Examiner* — Carol M Koslow
(74) *Attorney, Agent, or Firm* — Shimokaji IP

(57) ABSTRACT

Disclosed is a double-center bipyridyl cationic ion liquid prepared by reacting bipyridyl with haloalkane for synthesis of dialkyl bipyridyl halide, and converting the halogen ion in the dialkyl bipyridyl halide to the target anion via an ion-exchange reaction, to give the final target ionic liquid. Also disclosed are an organic electrolyte containing the double-center bipyridyl cationic ion liquid and a preparation method therefor.

9 Claims, 1 Drawing Sheet

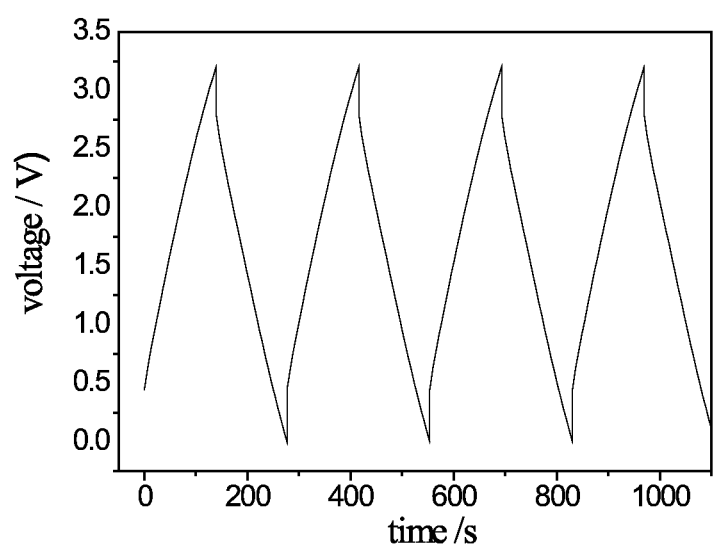

DOUBLE-CENTER BIPYRIDYL CATIONIC ION LIQUID, PREPARATION METHOD THEREFOR AND USE THEREOF

FIELD OF THE INVENTION

The present invention relates to ionic liquid, particularly to a double-center bipyridyl cationic ion liquid, preparation method thereof, an electrolyte comprising the same, and preparation method thereof.

BACKGROUND OF THE INVENTION

Ionic liquids are in the liquid state at room temperature range (generally below 100° C.), which consist of organic cations and inorganic anions (or organic anions). Ionic liquids which are regulable have been recognized as designer solvents, because ionic structure may be changed as needed by designer. The first ionic liquid, ethylamine nitrate was discovered as early as 1914. However, development in this field has been slowing down after the first discovery. Until 1992, when Wikes's team successfully synthesized 1-ethyl-3-methyl imidazolium tetrafluoroborates ionic liquid ([EMIM] $BF_4$) having low melting point, resistance to hydrolyzation, and good stability, studies on ionic liquids were developed rapidly. Since then a series of ionic liquids systems have been developed. Ionic liquids are primarily used for electrochemical investigation purpose. Recently, ionic liquids have drawn more public attention because ionic liquids can be used as green solvents for organic and macromolecular synthesis.

Compared to conventional organic solvent and electrolyte, ionic liquids exhibit a range of advantageous properties such as (1) having a melting point below or near room temperature, being liquid in a wide temperature range; (2) having a low vapor pressure, being non-volatile, colorless and odorless; (3) having a wide and stable temperature range, good chemical stability and wide electrochemical potential window range; (4) having a excellent solubility, can dissolve lots of inorganics and organics (5) having no ignition point, and being non-flammable; (6) can be recycled, environmentally friendly. So ionic liquids are promising electrolytes for double-layer capacitors.

Traditional electrolytes are prone to decompose at high voltage, causing a sharp rise of internal resistance and a rapid fall of capacitance. Therefore stability of electrolyte has always been the critical factor in specific energy of capacitor.

SUMMARY OF THE INVENTION

In view of this, it is necessary to provide double-center bipyridyl cationic ion liquid of resistance to decomposition at high voltage.

In addition, it is also necessary to provide a method for preparing the double-center bipyridyl cationic ion liquid.

In addition, it is also necessary to provide a method for preparing organic electrolyte comprising the double-center bipyridyl cationic ion liquid, and preparation method thereof.

A double-center bipyridyl cationic ion liquid having the following structural formula:

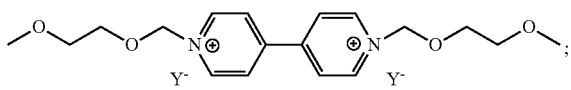

wherein $Y^-$ is $BF_4^-$, $PF_6^-$, $(CF_3SO_2)_2N^-$ or $(FSO_2)_2N^-$.

A method for preparing double-center bipyridyl cationic ion liquid, comprising:
- step 1: in atmosphere of protective gas, mixing bipyridine with haloalkane according to molar ratio of 1:2~1:2.5, heating to 60~80° C.; reacting while stirring to obtain dialkyl bipyridyl halide; wherein said haloalkane is methoxyethoxymethyl chloride or methoxyethoxymethyl bromide;
- step 2: mixing the dialkyl bipyridyl halide prepared in step 1 with salt having a formula of $M^+Y^-$ in a molar ratio of 1:2, then adding into deionized water; carrying out an ion exchange reaction while stirring; then obtaining a double-center bipyridyl cationic ion liquid having the following structural formula:

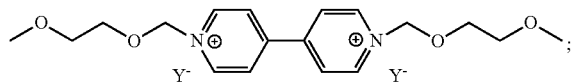

wherein $M^+$ is $Na^+$, $K^+$ or $NH_4^+$, $Y^-$ is $BF_4^-$, $PF_6^-$, $(CF_3SO_2)_2N^-$ or $(FSO_2)_2N^-$.

Preferably, in step 1, the step of reacting bipyridine with haloalkane is carried out for 24~72 h; reaction liquid is cooled and then washed with ethyl acetate to get washed matter; the washed matter is dried under vacuum to obtain purified dialkyl bipyridyl halide.

Preferably, in step 1, atmosphere of protective gas is nitrogen or argon.

Preferably, the ion exchange reaction of step 2 is carried out at room temperature for 8~24 h.

Preferably, step 2 further comprises purification of double-center bipyridyl cationic ion liquid, comprising:
- subjecting mixed liquid obtained after the reaction of dialkyl bipyridyl halide with salt having a formula of $M^+Y^-$ to extraction with dichloromethane to get aqueous phase, until no precipitation occurs in the aqueous phase when saturated aqueous solution of $AgNO_3$ is added;
- evaporating and concentrating extracts in dichloromethane then drying under vacuum to obtain purified double-center bipyridyl cationic ion liquid.

An organic electrolyte, comprising double-center bipyridyl cationic ion liquid, organic solvent and lithium salt, wherein said double-center bipyridyl cationic ion liquid has the following structural formula:

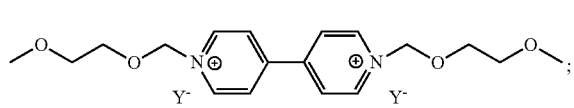

wherein $Y^-$ is $BF_4^-$, $PF_6^-$, $(CF_3SO_2)_2N^-$ or $(FSO_2)_2N^-$, mass ratio of said organic solvent to said double-center bipyridyl cationic ion liquid is in the range of 0~100, concentration of said lithium salt is in the range of 0.3 mol/L~1.2 mol/L.

Preferably, lithium salt is at least one of lithium tetrafluoroborate, lithium hexafluorophosphate, lithium bis(trifluoromethanesulphonyl)imide and lithium bis(fluorosulfonyl)imide.

Preferably, organic solvent is at least one of ethylene carbonate, methyl ethyl carbonate, dimethyl carbonate and ethyl propionate.

A method for preparing organic electrolyte, comprising:

step 1: in atmosphere of protective gas, mixing bipyridine with haloalkane according to molar ratio of 1:2~1:2.5, heating to 60~80° C.; reacting while stirring to obtain dialkyl bipyridyl halide; wherein said haloalkane is methoxyethoxymethyl chloride or methoxyethoxymethyl bromide;

step 2: mixing the dialkyl bipyridyl halide prepared in step 1 with salt having a formula of $M^+Y^-$ in a molar ratio of 1:2, then adding into deionized water; carrying out an ion exchange reaction while stirring; then obtaining a double-center bipyridyl cationic ion liquid having the following structural formula:

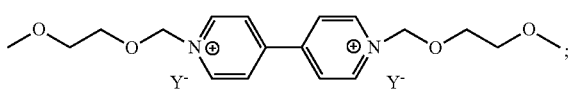

wherein $M^+$ is $Na^+$, $K^+$ or $NH_4^+$, $Y^-$ is $BF_4^-$, $PF_6^-$, $(CF_3SO_2)_2N^-$ or $(FSO_2)_2N^-$;

step 3: providing organic solvent, adding said double-center bipyridyl cationic ion liquid into said organic solvent while stirring uniformly; wherein mass ratio of said organic solvent to said double-center bipyridyl cationic ion liquid is in the range of 0~100;

step 4: adding lithium salt into mixed liquid of organic solvent and double-center bipyridyl cationic ion liquid; stirring to dissolve lithium salt then obtaining said organic electrolyte; wherein concentration of said lithium salt in organic electrolyte is in the range of 0.3~1.2 mol/L.

Electrochemical potential window range of such double-center bipyridyl cationic ion liquid is out of 4V, indicating good electrochemical stability, and resistance to decomposition at high voltage. Thus, organic electrolyte comprising such double-center bipyridyl cationic ion liquid has good stability at high charging voltage.

BRIEF DESCRIPTION OF THE DRAWINGS

The FIGURE is standard charge-discharge curve obtained by conducting conventional test on super capacitor comprising organic electrolyte prepared in Example 6 and electrode material.

DETAILED DESCRIPTION OF ILLUSTRATED EMBODIMENTS

Further description of double-center bipyridyl cationic ion liquid, preparation method thereof and use thereof will be illustrated, which combined with preferred embodiments and the drawings In one embodiment, double-center bipyridyl cationic ion liquid has the following structural formula:

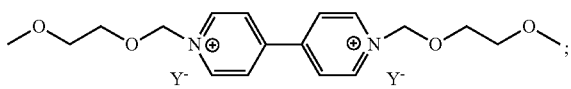

wherein $Y^-$ is $BF_4^-$, $PF_6^-$, $(CF_3SO_2)_2N^-$ or $(FSO_2)_2N^-$.

Electrochemical potential window range of such double-center bipyridyl cationic ion liquid is out of 4V, indicating good electrochemical stability, and resistance to decomposition at high voltage.

Alkoxyl structure is introduced into side chain of such double-center bipyridyl cationic ion liquid. Viscosity of ionic liquids is reduced. Besides, such oxygen-containing functional groups are beneficial for complexing with lithium ions in electrolyte and improvement of solubility of lithium salts.

Provided is a method for preparing the double-center bipyridyl cationic ion liquid, comprising:

step S11: in protective atmosphere of nitrogen or argon, mixing bipyridine with haloalkane according to molar ratio of 1:2~1:2.5, heating to 60~80° C.; reacting while stirring to obtain dialkyl bipyridyl halide;

The reaction equation is:

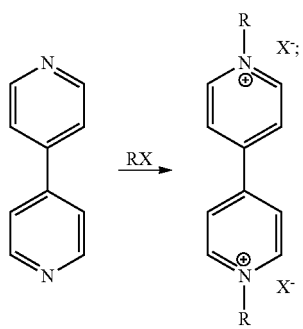

RX is meant to be haloalkane.

Purified dialkyl bipyridyl halide is obtained by drying washed matter under vacuum at 80° C. for 48 h.

Haloalkane can be methoxyethoxymethyl chloride

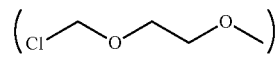

or methoxyethoxymethyl bromide

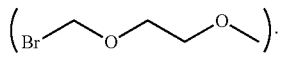

Reaction can be conducted and stirred for 24~72 h. Generally, double-center bipyridyl cationic ion liquid should react with haloalkane completely.

The reaction between bipyridine and haloalkane is not limited to conduct in protective atmosphere of nitrogen or argon, any inert gas may also be employed.

The purification of dialkyl bipyridyl halide is carried out by washing cooled reaction liquid with ethyl acetate for three times, but not limited to, other methods in the art may also be employed to purify dialkyl bipyridyl halide.

Step S12: mixing the dialkyl bipyridyl halide prepared in S11 with salt having a formula of $M^+Y^-$ in a molar ratio of 1:2, then adding into deionized water; reacting at room temperature for 8~24 h; subjecting mixed liquid obtained after the ion exchange reaction of dialkyl bipyridyl halide with salt having a formula of $M^+Y^-$ to extraction with dichloromethane to get aqueous phase, until no precipitation occurs in the aqueous phase when saturated aqueous solution of $AgNO_3$ is added; evaporating and concentrating extracts in dichloromethane then drying under vacuum at 80° C. for 48 h to obtain purified double-center bipyridyl cationic ion liquid;

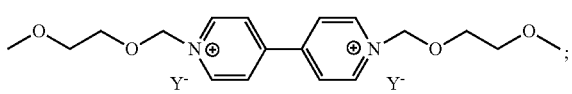

wherein $M^+$ is $Na^+$, $K^+$ or $NH_4^+$, $Y^-$ is $BF_4^-$, $PF_6^-$, $(CF_3SO_2)_2N^-$ or $(FSO_2)_2N^-$.

The reaction equation is:

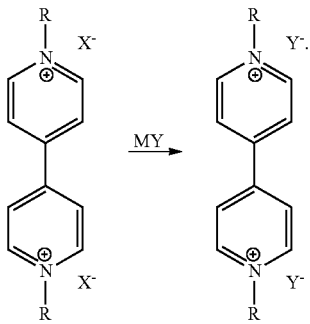

It will be understood that, the time of ion exchange reaction is not limited to 8~24 h, but dialkyl bipyridyl halide should react with salt having a formula of $M^+Y^-$ completely; other commonly encountered solvents or methods in the art may also be employed to separate and purify double-center bipyridyl cationic ion liquid.

Preparation method of the double-center bipyridyl cationic ion liquid is simple, and solvent of low toxicity is used during the process. So the preparation is low-cost, a large scale preparation can be easily achieved.

In one embodiment, organic electrolyte comprises double-center bipyridyl cationic ion liquid, organic solvent and lithium salt.

Double-center bipyridyl cationic ion liquid having the following structural formula:

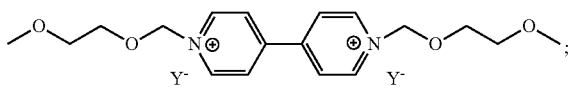

wherein $Y^-$ is $BF_4^-$, $PF_6^-$, $(CF_3SO_2)_2N^-$ or $(FSO_2)_2N^-$.

Mass ratio of organic solvent to double-center bipyridyl cationic ion liquid is greater than or equal to 0 and less than or equal to 100. Organic solvent can be at least one of ethylene carbonate, ethyl methyl carbonate, dimethyl carbonate and ethyl propionate (EP).

Concentration of lithium salt in organic electrolyte is in the range of 0.3~1.2 mol/L.

In some preferred embodiments, concentration of lithium salt in organic electrolyte is 1 mol/L.

Lithium salt can be at least one of lithium tetrafluoroborate ($LiBF_4$), lithium hexafluorophosphate ($LiPF_6$), lithium bis(trifluoromethanesulphonyl)imide (LiTFSI) and lithium bis(fluorosulfonyl)imide (LiFSI).

Provided is a method for preparing the electrolyte, comprising:

S21: in protective atmosphere of nitrogen or argon, mixing bipyridine with haloalkane according to molar ratio of 1:2~1:2.5, heating to 60~80° C.; reacting while stirring to obtain dialkyl bipyridyl halide;

Purified dialkyl bipyridyl halide is obtained by drying washed matter under vacuum at 80° C. for 48 h.

Haloalkane can be methoxyethoxymethyl chloride

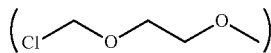

or methoxyethoxymethyl bromide

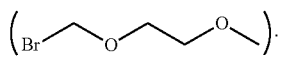

Reaction can be conducted and stirred for 24~72 h. Generally, double-center bipyridyl cationic ion liquid should react with haloalkane completely.

The reaction between bipyridine and haloalkane is not limited to conduct in protective atmosphere of nitrogen or argon, any inert gas may also be employed.

The purification of dialkyl bipyridyl halide is carried out by washing cooled reaction liquid with ethyl acetate for three times, but not limited to, other methods in the art may also be employed to purify dialkyl bipyridyl halide.

S22: mixing the dialkyl bipyridyl halide prepared in step S21 with salt having a formula of $M^+Y^-$ in a molar ratio of 1:2, then adding into deionized water; reacting at room temperature for 8~24 h; subjecting mixed liquid obtained after the ion exchange reaction of dialkyl bipyridyl halide with salt having a formula of $M^+Y^-$ to extraction with dichloromethane to get aqueous phase, until no precipitation occurs in the aqueous phase when saturated aqueous solution of $AgNO_3$ is added; evaporating and concentrating extracts in dichloromethane then drying under vacuum at 80° C. for 48 h to obtain purified double-center bipyridyl cationic ion liquid;

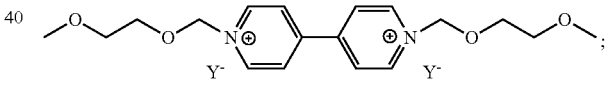

wherein $M^+$ is $Na^+$, $K^+$ or $NH_4^+$, $Y^-$ is $BF_4^-$, $PF_6^-$, $(CF_3SO_2)_2N^-$ or $(FSO_2)_2N^-$.

It will be understood that, the time of ion exchange reaction is not limited to 8~24 h, but dialkyl bipyridyl halide should react with salt having a formula of $M^+Y^-$ completely; other commonly encountered solvents or methods in the art may also be employed to separate and purify double-center bipyridyl cationic ion liquid.

S23: providing organic solvent, adding double-center bipyridyl cationic ion liquid into organic solvent while stirring uniformly; wherein mass ratio of organic solvent to double-center bipyridyl cationic ion liquid is in the range of 0~100;

Organic solvent is at least one of ethylene carbonate, methyl ethyl carbonate, dimethyl carbonate and ethyl propionate (EP).

Preferably, Step S23 is carried out under the protection of inert gas, the inert gas can be nitrogen or argon.

S24: adding lithium salt into mixed liquid of organic solvent and double-center bipyridyl cationic ion liquid; stirring to dissolve lithium salt then obtaining organic electrolyte.

Concentration of lithium salt in organic electrolyte is in the range of 0.3~1.2 mol/L.

In some preferred embodiments, concentration of lithium salt is 1 mol/L.

Lithium salt can be at least one of lithium tetrafluoroborate (LiBF$_4$), lithium hexafluorophosphate (LiPF$_6$), lithium bis(trifluoromethanesulphonyl)imide (LiTFSI) and lithium bis(fluorosulfonyl)imide (LiFSI).

Electrochemical potential window range of such double-center bipyridyl cationic ion liquid is out of 4V, indicating good electrochemical stability, and resistance to decomposition at high voltage, thus, organic electrolyte comprising such double-center bipyridyl cationic ion liquid has good stability at high charging voltage. Lithium salt provides lithium ions when employed in lithium ion batteries or lithium ion capacitors, while organic solvent could reduce viscosity of electrolyte.

The present invention will be described below in detail referring to preferred embodiments.

Example 1

Synthesis of Double-Center Bipyridyl Tetrafluoroborate

To a 250-mL flask, 1 mol of bipyridine and 2.1 mol of methoxyethoxymethyl chloride were added separately. In the protective atmosphere of N$_2$, temperature was elevated to 70° C. The reaction was started and stirred for 36 h. After being allowed to stand and cool down, the reaction mixture was washed with ethyl acetate for three times. Drying under vacuum at 80° C., light yellow solid, i.e. dialkyl bipyridyl chloride was obtained in a yield of 78%.

To a 500-mL flask, 0.5 mol of dialkyl bipyridyl chloride, 1 mol of NaBF$_4$ and 120 mL of deionized water were added at room temperature while stirring for 16-24 h. After the reaction, mixed liquid was subjected to extraction with 250 mL of dichloromethane for three times, liquid extracts were combined. Then back-extracted with 60 mL of deionized water each time to get aqueous phase, until no further precipitation occurs in the aqueous phase when saturated aqueous solution of AgNO$_3$ was added. Dichloromethane phase was evaporated and concentrated by rotary evaporator then dried under vacuum at 80° C. for 48 h to give light yellow solid, i.e. double-center bipyridyl tetrafluoroborate.

Hydrogen-1 nuclear magnetic resonance (NMR) spectrum of double-center bipyridyl tetrafluoroborate of this embodiment shows: $^1$H NMR ((CD$_3$)$_2$CO, 400 MHz, ppm): 8.69 (d, 4H), 7.63 (d, 4H), 5.92 (s, 4H), 3.64 (m, 8H), 3.24 (s, 6H).

Example 2

Synthesis of Double-Center Bipyridyl Hexafluorophosphate

To a 250-mL flask, 1 mol of bipyridine and 2.1 mol of methoxyethoxymethyl bromide were added separately. In the protective atmosphere of Are, temperature was elevated to 70° C. The reaction was started and stirred for 36 h. After being allowed to stand and cool down, the reaction mixture was washed with ethyl acetate for three times. Drying under vacuum at 80° C., light yellow solid, i.e. dialkyl bipyridyl bromide was obtained in a yield of 80%.

To a 500-mL flask, 0.5 mol of dialkyl bipyridyl bromide, 1 mol of KPF$_6$ and 120 mL of deionized water were added at room temperature while stirring for 16 h. After the reaction, mixed liquid was subjected to extraction with 250 mL of dichloromethane for three times, liquid extracts were combined. Then back-extracted with 60 mL of deionized water each time to get aqueous phase, until no further precipitation occurs in the aqueous phase when saturated aqueous solution of AgNO$_3$ was added. Dichloromethane phase was evaporated and concentrated by rotary evaporator then dried under vacuum at 80° C. for 48 h to give light yellow solid, i.e. double-center bipyridyl hexafluorophosphate.

Hydrogen-1 nuclear magnetic resonance (NMR) spectrum of double-center bipyridyl hexafluorophosphate of this embodiment shows: $^1$H NMR ((CD$_3$)$_2$CO, 400 MHz, ppm): 8.70 (d, 4H), 7.63 (d, 4H), 5.93 (s, 4H), 3.64 (m, 8H), 3.25 (s, 6H).

Example 3

Synthesis of Double-Center Bipyridyl Trifluoromethylsulfonyl Imide

To a 500-mL flask, 0.5 mol of dialkyl bipyridyl chloride (prepared in Example 1), 1 mol of potassium trifluoromethanesulfonyl imide (KTFSI), and 120 mL of deionized water were added at room temperature while stirring for 16 h. After the reaction, mixed liquid was subjected to extraction with 250 mL of dichloromethane for three times, liquid extracts were combined. Then back-extracted with 60 mL of deionized water each time to get aqueous phase, until no further precipitation occurs in the aqueous phase when saturated aqueous solution of AgNO$_3$ was added. Dichloromethane phase was evaporated and concentrated by rotary evaporator then dried under vacuum at 80° C. for 48 h to give light yellow solid, i.e. double-center bipyridyl trifluoromethylsulfonyl imide.

Hydrogen-1 nuclear magnetic resonance (NMR) spectrum of double-center bipyridyl trifluoromethylsulfonyl imide of this embodiment shows: $^1$H NMR ((CD$_3$)$_2$CO, 400 MHz, ppm): 8.71 (d, 4H), 7.65 (d, 4H), 5.95 (s, 4H), 3.66 (m, 8H), 3.26 (s, 6H).

Example 4

Synthesis of Double-Center Bipyridyl Trifluoromethansulphonate

To a 500-mL flask, 0.5 mol of dialkyl bipyridyl bromide (prepared in Example 2), 1 mol of CF$_3$SO$_3$Na and 120 mL of deionized water were added at room temperature while stirring for 16 h. After the reaction, mixed liquid was subjected to extraction with 250 mL of dichloromethane for three times, liquid extracts were combined. Then back-extracted with 60 mL of deionized water each time to get aqueous phase, until no further precipitation occurs in the aqueous phase when saturated aqueous solution of AgNO$_3$ was added. Dichloromethane phase was evaporated and concentrated by rotary evaporator then dried under vacuum at 80° C. for 48 h to give light yellow solid, i.e. double-center bipyridyl trifluoromethansulphonate.

Hydrogen-1 nuclear magnetic resonance (NMR) spectrum of double-center bipyridyl trifluoromethansulphonate of this embodiment shows: $^1$H NMR ((CD$_3$)$_2$CO, 400 MHz, ppm): 8.70 (d, 4H), 7.63 (d, 4H), 5.93 (s, 4H), 3.65 (m, 8H), 3.23 (s, 6H).

Example 5

Synthesis of Double-Center Bipyridyl Bis(Fluorosulfonyl)Imide

See Example 1 for preparation details. 1 mol of NaBF$_4$ was replaced with 1 mol of potassium bis(fluorosulfonyl)imide ((FSO$_2$)$_2$NK).

Hydrogen-1 nuclear magnetic resonance (NMR) spectrum of double-center bipyridyl bis(fluorosulfonyl)imide of this embodiment shows: $^1$H NMR ((CD$_3$)$_2$CO, 400 MHz, ppm): 8.70 (d, 4H), 7.64 (d, 4H), 5.92 (s, 4H), 3.66 (m, 8H), 3.25 (s, 6H).

Example 6

In protective atmosphere of N$_2$, organic solvent was prepared by mixing ethylene carbonate (EC), ethyl methyl carbonate (EMC), dimethyl carbonate (DMC) and ethyl propionate (EP) in a molar ratio of 2:5:2:3 (abbr. mixed solvent$_{EC+EMC+DMC+EP}$). Double-center bipyridyl tetrafluoroborate (prepared in Example 1) ionic liquid was added according to the mass ratio of mixed solvent$_{EC+EMC+DMC+EP}$:double-center bipyridyl ionic liquid=10:1. The mixture was heated to 40° C. and stirred to get uniform organic phase. At last, a certain amount of lithium salt (LiBF$_4$ in this embodiment) was added, the molar concentration of lithium salt was 1 mol/L (amount of lithium salt was determined by volume of organic phase V$_{EC+EMC+DMC+EP+double\text{-}center\ bipyridyl\ ionic\ liquid}$). Lithium salt was completely dissolved by stirring constantly. The desired organic electrolyte was obtained.

The FIGURE is charge-discharge curve of button cell comprising graphene as electrode material and organic electrolyte prepared in this embodiment. The charge-discharge test was performed on a CHI660A electrochemical workstation at a constant current 0.25 A/g. The electrochemical potential window ranges from 0 to 3.2V.

It can be seen from the FIGURE that electrolyte as prepared in this embodiment is suitable for super capacitors, and electrolyte has good stability at a charging voltage of 3.2 V.

Example 7

In protective atmosphere of Ar$_2$, 100 mL of double-center bipyridyl hexafluorophosphate (prepared in Example 2) ionic liquid was added and heated to 40° C. while stirring. A certain amount of lithium salt (LiPF$_6$ in this embodiment) was added, the molar concentration of lithium salt was 0.3 mol/L. Lithium salt was completely dissolved by stirring constantly. The desired organic electrolyte was obtained.

Example 8

In protective atmosphere of N$_2$, organic solvent was prepared by mixing ethylene carbonate (EC), ethyl methyl carbonate (EMC), dimethyl carbonate (DMC) and ethyl propionate (EP) in a molar ratio of 2:5:2:3 (abbr. mixed solvent$_{EC+EMC+DMC+EP}$). Double-center bipyridyl bis(trifluoromethylsulfonyl)imide (prepared in Example 3) ionic liquid was added according to the mass ratio of mixed solvent$_{EC+EMC+DMC+EP}$:double-center bipyridyl ionic liquid=1:100. The mixture was heated to 40° C. and stirred to get uniform organic phase. At last, a certain amount of lithium salt (LiTFSI in this embodiment) was added, the molar concentration of lithium salt was 0.5 mol/L (amount of lithium salt was determined by volume of organic phase V$_{EC+EMC+DMC+EP+double\text{-}center\ bipyridyl\ ionic\ liquid}$). Lithium salt was completely dissolved by stirring constantly. The desired organic electrolyte was obtained.

Example 9

In protective atmosphere of Ar$_2$, organic solvent was prepared by mixing ethylene carbonate (EC), ethyl methyl carbonate (EMC), dimethyl carbonate (DMC) and ethyl propionate (EP) in a molar ratio of 2:5:2:3 (abbr. mixed solvent$_{EC+EMC+DMC+EP}$). Double-center bipyridyl bis(fluorosulfonyl)imide (prepared in Example 4) ionic liquid was added according to the mass ratio of mixed solvent$_{EC+EMC+DMC+EP}$:double-center bipyridyl ionic liquid=1:10. The mixture was heated to 40° C. and stirred to get uniform organic phase. At last, a certain amount of lithium salt (LiFSI in this embodiment) was added, the molar concentration of lithium salt was 0.7 mol/L (amount of lithium salt was determined by volume of organic phase V$_{EC+EMC+DMC+EP+double\text{-}center\ bipyridyl\ ionic\ liquid}$). Lithium salt was completely dissolved by stirring constantly. The desired organic electrolyte was obtained.

Example 10

In protective atmosphere of N$_2$, organic solvent was prepared by mixing ethylene carbonate (EC), ethyl methyl carbonate (EMC), dimethyl carbonate (DMC) and ethyl propionate (EP) in a molar ratio of 2:5:2:3 (abbr. mixed solvent$_{EC+EMC+DMC+EP}$). Double-center bipyridyl tetrafluoroborate ionic liquid was added according to the mass ratio of mixed solvent$_{EC+EMC+DMC+EP}$:double-center bipyridyl ionic liquid=1:1. The mixture was heated to 40° C. and stirred to get uniform organic phase. At last, a certain amount of lithium salt (in this embodiment, mixture of LiBF$_4$ and LiPF$_6$ in a molar ratio of 1:1) was added, the molar concentration of lithium salt was 0.9 mol/L (amount of lithium salt was determined by volume of organic phase V$_{EC+EMC+DMC+EP+double\text{-}center\ bipyridyl\ ionic\ liquid}$). Lithium salt was completely dissolved by stirring constantly. The desired organic electrolyte was obtained.

Example 11

In protective atmosphere of Ar$_2$, organic solvent was prepared by mixing ethylene carbonate (EC), ethyl methyl carbonate (EMC), dimethyl carbonate (DMC) and ethyl propionate (EP) in a molar ratio of 2:5:2:3 (abbr. mixed solvent$_{EC+EMC+DMC+EP}$). Double-center bipyridyl ionic liquid (in this embodiment, mixture of double-center bipyridyl tetrafluoroborate and double-center bipyridyl hexafluorophosphate in a molar ratio of 1:1) was added according to the mass ratio of mixed solvent$_{EC+EMC+DMC+EP}$:double-center bipyridyl ionic liquid=40:1. The mixture was heated to 40° C. and stirred to get uniform organic phase. At last, a certain amount of lithium salt (in this embodiment, mixture of LiTFSI and LiFSI in a molar ratio of 1:1) was added, the molar concentration of lithium salt was 1 mol/L (amount of lithium salt was determined by volume of organic phase V$_{EC+EMC+DMC+EP+double\text{-}center\ bipyridyl\ ionic\ liquid}$). Lithium salt was completely dissolved by stirring constantly. The desired organic electrolyte was obtained.

Example 12

In protective atmosphere of Ar$_2$, organic solvent was prepared by mixing ethylene carbonate (EC), ethyl methyl carbonate (EMC), dimethyl carbonate (DMC) and ethyl propionate (EP) in a molar ratio of 2:5:2:3 (abbr. mixed solvent$_{EC+EMC+DMC+EP}$). Double-center bipyridyl ionic liquid (in this embodiment, mixture of double-center bipyridyl bis(trifluoromethylsulfonyl)imide and double-center bipyridyl bis(fluorosulfonyl)imide in a molar ratio of 1:1) was added according to the mass ratio of mixed solvent$_{EC+EMC+DMC+EP}$:double-center bipyridyl ionic liquid=70:1. The mixture was heated to 40° C. and stirred to get uniform organic phase. At last, a certain amount of lithium salt (in this embodiment, mixture of LiPF6 and LiTFSI in a molar ratio of 1:1) was added, the molar concentration of lithium salt was 1.1 mol/L (amount of lithium salt was determined by volume of organic phase $V_{EC+EMC+DMC+EP+double\text{-}center\ bipyridyl\ ionic\ liquid}$). Lithium salt was completely dissolved by stirring constantly. The desired organic electrolyte was obtained.

Example 13

In protective atmosphere of $N_2$, organic solvent was prepared by mixing ethylene carbonate (EC), ethyl methyl carbonate (EMC), dimethyl carbonate (DMC) and ethyl propionate (EP) in a molar ratio of 2:5:2:3 (abbr. mixed solvent$_{EC+EMC+DMC+EP}$). Double-center bipyridyl bis(trifluoromethylsulfonyl)imid ionic liquid was added according to the mass ratio of mixed solvent$_{EC+EMC+DMC+EP}$:double-center bipyridyl ionic liquid=100:1. The mixture was heated to 40° C. and stirred to get uniform organic phase. At last, a certain amount of lithium salt (LiTFSI in this embodiment) was added, the molar concentration of lithium salt was 1.2 mol/L (amount of lithium salt was determined by volume of organic phase $V_{EC+EMC+DMC+EP+double\text{-}center\ bipyridyl\ ionic\ liquid}$). Lithium salt was completely dissolved by stirring constantly. The desired organic electrolyte was obtained.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. A double-center bipyridyl cationic ion liquid having the following structural formula:

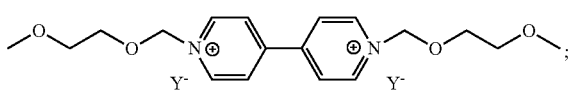

wherein $Y^-$ is $BF_4^-$, $PF_6^-$, $(CF_3SO_2)_2N^-$ or $(FSO_2)_2N^-$.

2. A method for preparing double-center bipyridyl cationic ion liquid, comprising:
step 1: in atmosphere of protective gas, mixing bipyridine with haloalkane according to molar ratio of 1:2~1:2.5, heating to 60~80° C.; reacting while stirring to obtain dialkyl bipyridyl halide; wherein said haloalkane is methoxyethoxymethyl chloride or methoxyethoxymethyl bromide;
step 2: mixing the dialkyl bipyridyl halide prepared in step 1 with salt having a formula of $M^+Y^-$ in a molar ratio of 1:2, then adding into deionized water; carrying out an ion exchange reaction while stirring; then obtaining a double-center bipyridyl cationic ion liquid having the following structural formula:

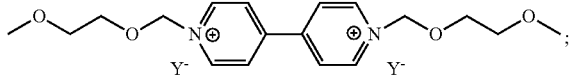

wherein $M^+$ is $Na^+$, $K^+$ or $NH_4^+$, $Y^-$ is $BF_4^-$, $PF_6^-$, $(CF_3SO_2)_2N^-$ or $(FSO_2)_2N^-$.

3. The method for preparing double-center bipyridyl cationic ion liquid according to claim 2, wherein in step 1, the step of reacting said bipyridine with haloalkane is carried out for 24~72 h; reaction liquid is cooled and then washed with ethyl acetate to get washed matter; the washed matter is dried under vacuum to obtain purified dialkyl bipyridyl halide.

4. The method for preparing double-center bipyridyl cationic ion liquid according to claim 2, wherein in step 1 said atmosphere of protective gas is nitrogen or argon.

5. The method for preparing double-center bipyridyl cationic ion liquid according to claim 2, wherein in step 2, the ion exchange reaction is carried out at room temperature for 8~24 h.

6. The method for preparing double-center bipyridyl cationic ion liquid according to claim 2, wherein step 2 further comprises purification of said double-center bipyridyl cationic ion liquid, comprising:
subjecting mixed liquid obtained after the reaction of dialkyl bipyridyl halide with salt having a formula of $M^+Y^-$ to extraction with dichloromethane to get aqueous phase, until no precipitation occurs in the aqueous phase when saturated aqueous solution of $AgNO_3$ is added;
evaporating and concentrating extracts in dichloromethane then drying under vacuum to obtain purified double-center bipyridyl cationic ion liquid.

7. An organic electrolyte, comprising double-center bipyridyl cationic ion liquid, organic solvent and lithium salt, wherein said double-center bipyridyl cationic ion liquid has the following structural formula:

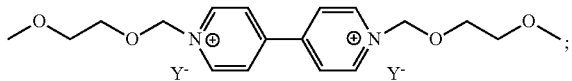

wherein $Y^-$ is $BF_4^-$, $PF_6^-$, $(CF_3SO_2)_2N^-$ or $(FSO_2)_2N^-$, mass ratio of said organic solvent to said double-center bipyridyl cationic ion liquid is in the range of 0~100, concentration of said lithium salt is in the range of 0.3 mol/L~1.2 mol/L.

8. The organic electrolyte according to claim 7, wherein said lithium salt is at least one of lithium tetrafluoroborate, lithium hexafluorophosphate, lithium bis(trifluoromethanesulphonyl)imide and lithium bis(fluorosulfonyl)imide.

9. The organic electrolyte according to claim 7, wherein said organic solvent is at least one of ethylene carbonate, ethyl methyl carbonate, dimethyl carbonate and ethyl propionate.

* * * * *